(12) United States Patent
Borgmeier et al.

(10) Patent No.: US 11,247,967 B2
(45) Date of Patent: Feb. 15, 2022

(54) PROCESS FOR THE MANUFACTURING OF ALKANESULFONIC ACIDS

(71) Applicant: BASF SE, Ludwigshafen am Rhein (DE)

(72) Inventors: Frieder Borgmeier, Ludwigshafen (DE); Jan Spielmann, Ludwigshafen (DE); Michael Zeilinger, Ludwigshafen (DE); Juergen Wortmann, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/963,748

(22) PCT Filed: Jan. 30, 2019

(86) PCT No.: PCT/EP2019/052199
§ 371 (c)(1),
(2) Date: Jul. 21, 2020

(87) PCT Pub. No.: WO2019/154681
PCT Pub. Date: Aug. 15, 2019

(65) Prior Publication Data
US 2021/0094908 A1 Apr. 1, 2021

(30) Foreign Application Priority Data
Feb. 7, 2018 (EP) ..................................... 18155580

(51) Int. Cl.
*C07C 303/14* (2006.01)
*C07C 303/44* (2006.01)

(52) U.S. Cl.
CPC .......... *C07C 303/14* (2013.01); *C07C 303/44* (2013.01)

(58) Field of Classification Search
CPC ... C07C 303/14; C07C 303/44; C07C 303/06; C07C 309/04
See application file for complete search history.

(56) References Cited

U.S. PATENT DOCUMENTS

| 4,035,242 | A | 7/1977 | Brandt |
| 4,450,047 | A | 5/1984 | Malzahn |
| 4,895,977 | A | 1/1990 | Nosowitz |
| 5,583,253 | A | 12/1996 | Henderson et al. |
| 6,207,025 | B1 | 3/2001 | Eiermann et al. |
| 6,531,629 | B1 | 3/2003 | Eiermann et al. |
| 2004/0103782 | A1* | 6/2004 | Wascheck ............ B01D 53/229 95/50 |
| 2005/0070614 | A1* | 3/2005 | Richards ............... C07C 303/06 518/700 |
| 2006/0100458 | A1 | 5/2006 | Sen et al. |
| 2016/0289181 | A1 | 10/2016 | Ott et al. |
| 2020/0095197 | A1* | 3/2020 | Richards ............... C07C 303/02 |

FOREIGN PATENT DOCUMENTS

| CN | 101875623 A | 11/2010 | |
| EP | 0 675 106 A1 | 10/1995 | |
| EP | 0 675 107 A1 | 10/1995 | |
| EP | 1 133 470 A1 | 9/2001 | |
| EP | 1 591 563 A1 | 11/2005 | |
| WO | WO 2004/041399 A2 | 5/2004 | |
| WO | WO 2005/069751 A2 | 8/2005 | |
| WO | WO 2015/071365 A1 | 5/2015 | |
| WO | WO2015/071455 | * 5/2015 | |
| WO | WO 2015/071455 | 5/2015 | |
| WO | WO 2018/146153 A1 | 8/2018 | |
| WO | WO-2018146153 A1 * | 8/2018 | ........... C07C 303/06 |

OTHER PUBLICATIONS 62601065 specification, 44 pages. (Year: 2017).*
62601065 Figure 8, 1 page (Year: 2017).*
EP17154935.5, 14 pages (Year: 2017).*
Karger et al. (Mixed Sulfonic-Carboxylic Anhydrides. I. Synthesis and Thermal Stability. New Syntheses of Sulfonic Anhydrides, JOC, vol. 36, No. 4, pp. 528-531, Published 1971) (Year: 1971).*
Crystallization (9 pages Published and last page revision 2011). (Year: 2011).*
International Search Report dated Apr. 4, 2019 in PCT/EP2019/052199 filed on Jan. 30, 2019.
International Preliminary Report on Patentability dated May 11, 2020 in PCT/EP2019/052199 filed on Jan. 30, 2019.
Extended European Search Report dated Jul. 26, 2018 in Patent Application No. 18155580.6, 3 pages.
Naomi Basickes, et al., "Radical-Initiated Functionalization of Methane and Ethane in Fuming Sulfuric Acid" Journal of the American Chemical Society, vol. 118, Issue 51, Dec. 25, 1996, pp. 13111-13112.

* cited by examiner

*Primary Examiner* — Yevgeny Valenrod
*Assistant Examiner* — Blaine G Doletski
(74) *Attorney, Agent, or Firm* — Arent Fox LLP

(57) ABSTRACT

A process for manufacturing of an alkanesulfonic acid, and an alkanesulfonic acid manufactured by the process. Aspects of the process may involve manufacturing an alkanesulfonic acid by reaction of an initiator composition with an alkane and sulfur trioxide by preparing an initiator composition by reacting aqueous hydrogen peroxide with alkanesulfonic acid and/or $H_2SO_4$; and reacting the initiator composition with sulfur trioxide and alkane to form an alkanesulfonic acid, wherein an alkane with a purity of at least 98.0 mol-% is used.

19 Claims, 4 Drawing Sheets

FIGURE 1: exemplary, schematic diagram of an embodiment of the process of the present invention
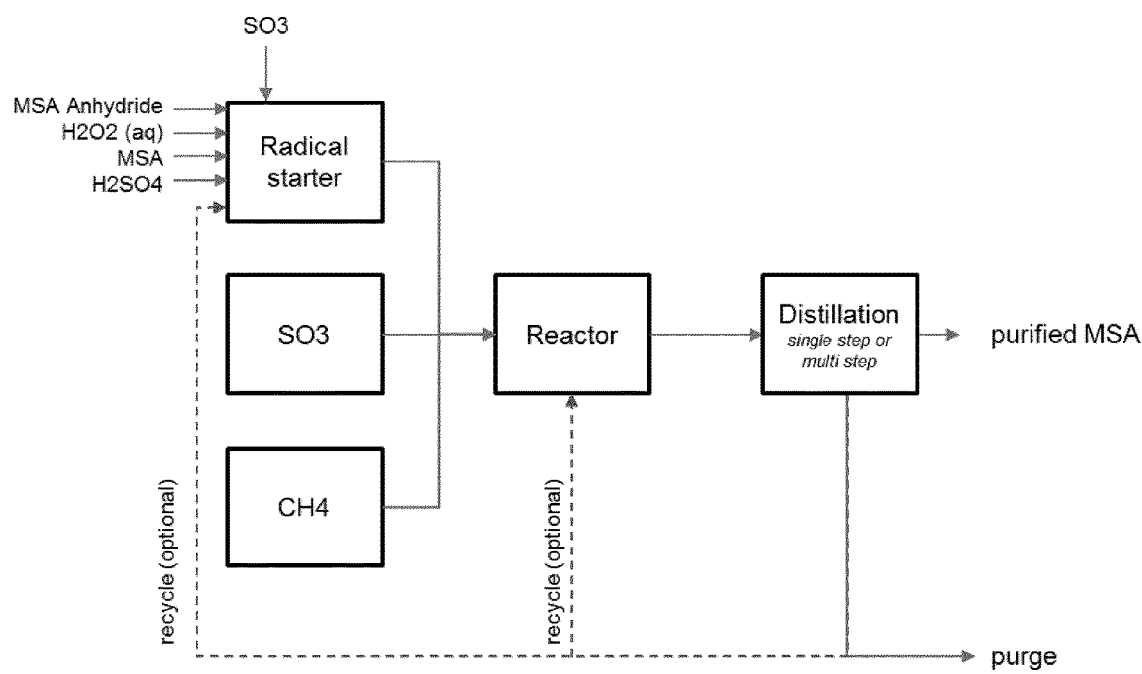

Figure 2. Reaction parameters according to example 1
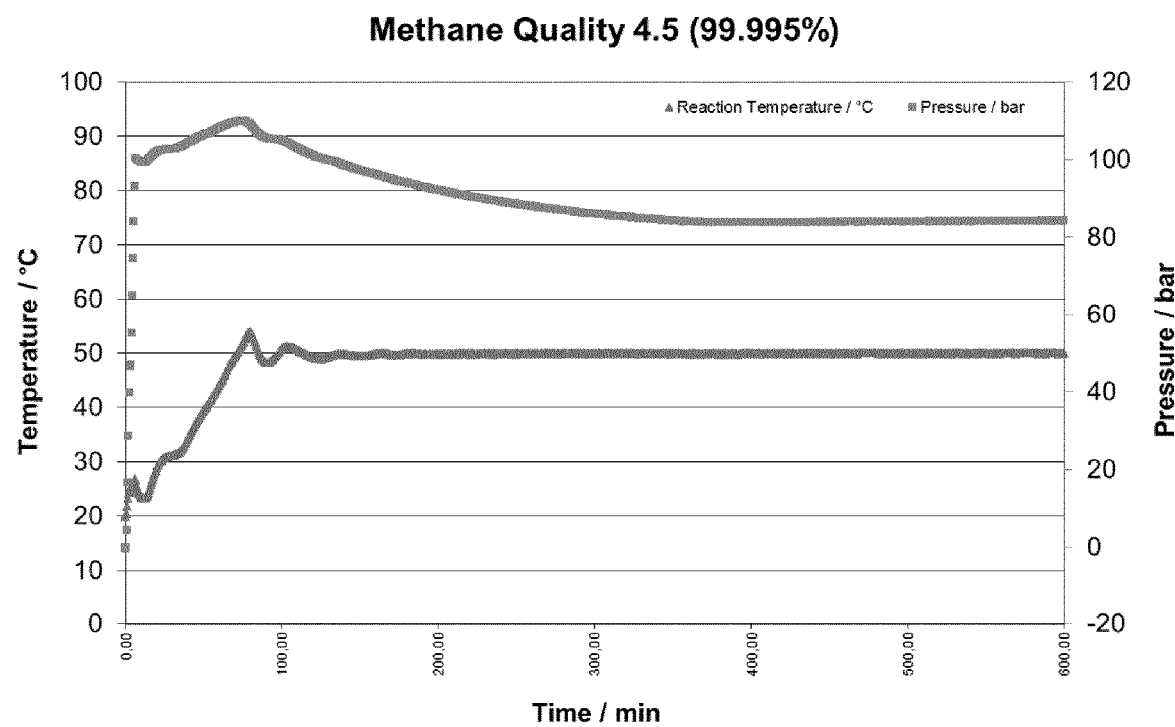

Figure 3 - Reaction parameters according to example 2
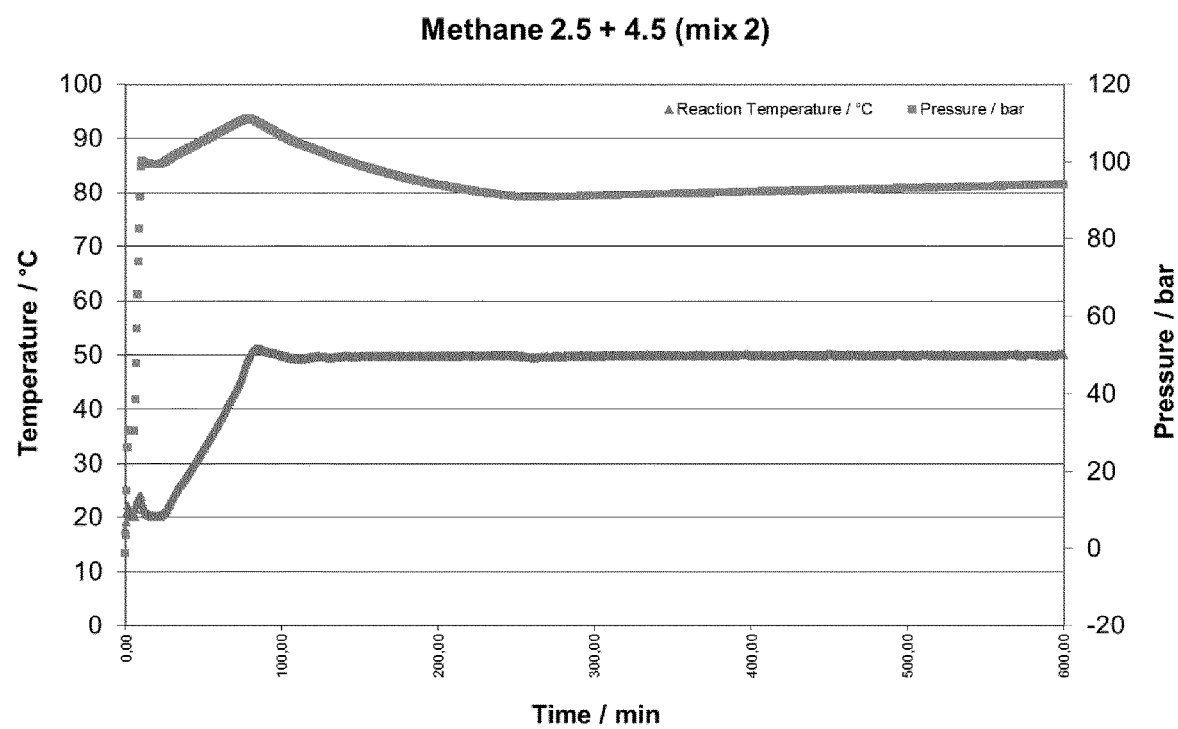

Figure 4 - Reaction parameters according to example 3
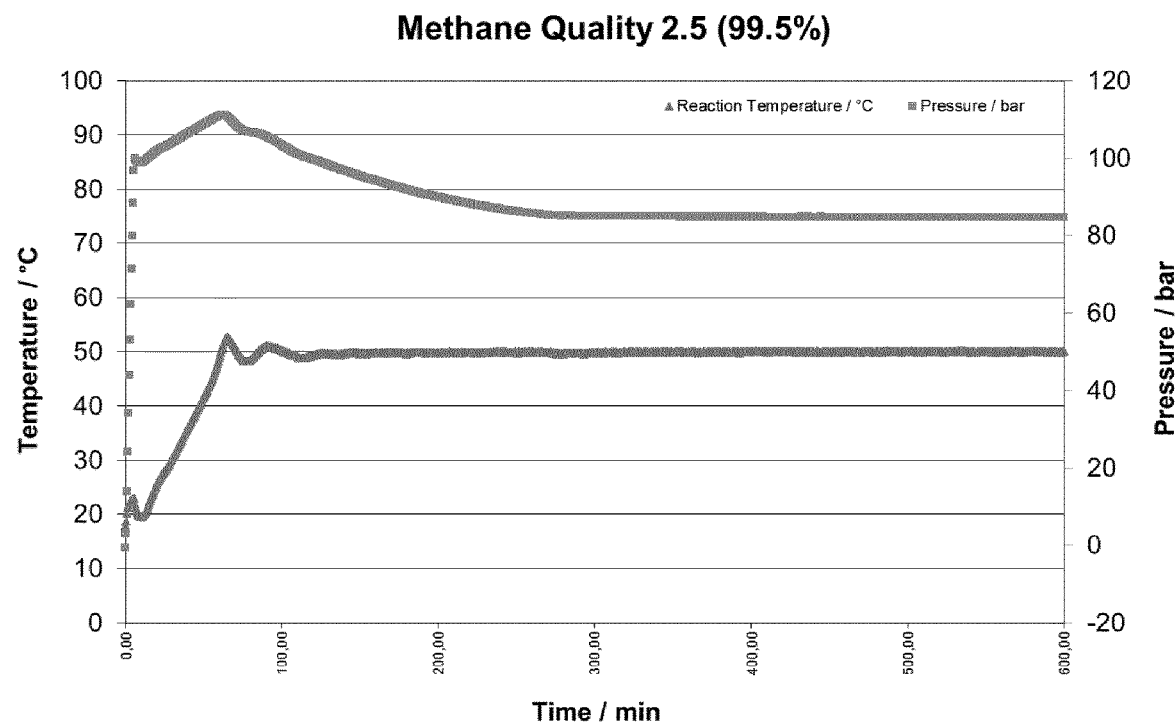

PROCESS FOR THE MANUFACTURING OF ALKANESULFONIC ACIDS

The present invention relates to a process for manufacturing of an alkanesulfonic acid, for example methanesulfonic acid (MSA), and to an alkanesulfonic acid manufactured by said process and its uses.

Methanesulphonic acid ($H_3CSO_3H$, MSA), like other alkanesulfonic acids, is a strong organic acid which is used for a multiplicity of different processes, for example for electroplating processes, in chemical synthesis or in cleaning applications, or for example in semiconductor industry or as rust and scale remover.

Several manufacturing technologies for alkanesulfonic acids (e.g. MSA) are described in the art. For example, MSA can be produced by oxidation of dimethyldisulfide or methylmercaptane with air (EP 1133470 B1) or by oxidation with chlorine in the presence of water (EP 675106, EP675107).

Another route describes the synthesis of MSA by reacting methane and SO3 as a simple and straight forward synthesis option.

For example, US 20060100458 discloses a reaction of methane and sulfur trioxide to methane sulfonic acid by adding a solution containing $H_2S_2O_8$ to a mixture consisting of sulfur trioxide dissolved in methane sulfonic acid. $H_2S_2O_8$ acts as initiator and is prepared by passing sulfur trioxide diluted with nitrogen gas through 70% aqueous hydrogen peroxide ($H_2O_2$). MSA yields up to 99% are achieved. MSA selectivities >99% are quoted while side products are formed with a selectivity of less than 1%, with side products typically being methyl/methoxy-sulfur-species as methylsulfate CH3OSO3H, dimethylsulfate (CH3O)2SO2, methylmethanesulfonate CH3SO3CH3 or methanedisulfonic acid CH2(SO3H)2.

WO2005/069751 discloses an anhydrous processing of methane into methane sulfonic acid by a radical process using Marshall's acid or Caro's acid to create methyl radicals, which form methane sulfonic acid by combination with sulfur trioxide. As alternative initiators to form methane radicals, methane sulfonic acid anhydride is disclosed. The reported yields are comparable to those in US 20060100458. Derived from computer modeling the formation of methylbisuflite as side product could not be ruled out but no evidence is given in the experimental section that such a compound could be analyzed by NMR spectroscopy. Beyond this one compound no other side products are described.

WO2004/041399 discloses an anhydrous processing of methane into methane sulfonic acid by a radical process to avoid the creation of waste and salts as byproducts in order to improve the selectivity and yield. No side products could be found in the NMR analysis of the MSA produced.

WO2015/071455 discloses the manufacture of MSA from methane using a mixed peroxide derived from sulfuric acid and methane sulfonic acid as radical starter or mixtures thereof as for example with sulfuric acid and/or methane sulfonic acid. According to the examples the reaction product contains ca. 42% MSA. No statements were done as to what the remaining 58% exactly consist of and if there were any impurities beyond sulfuric acid.

WO 2015/071365 A1 discloses a process for the manufacture of alkanesulfonic acids (e.g. MSA) from sulfur trioxide (SO3) and alkanes (e.g. methane) by using peroxides. It is assumed that the reaction follows a radical mechanism. MSA was obtained as clear colorless liquid that did not fume. In the NMR spectrum and with ion chromatography, only sulfuric acid and MSA could be detected. Processing of the MSA was effected by distillation but no information is given with regard to distillation conditions or purity of resulting MSA.

In most manufacturing processes for alkanesulfonic acids, like MSA, a downstream purification step, for example by distillation, is required in order to isolate and/or purify the final product. Potential sources for impurities might be impurities of the equipment used (e.g. metals by corrosion), side products generated in the course of the reaction via side reactions, impurities introduced via raw materials of insufficient purity etc.

Usually, the mixture of components leaving the reaction vessel and entering the purification step contains a high percentage of product (i.e. alkanesulfonic acid), but also some unreacted alkane and sulfur trioxide, along with sulfuric acid and other compounds such as alkanesulfonic acid anhydride, methionic acid etc. This purification step is typically realized in a distillation column. Alternatively, it can be done in a reaction vessel, in a crystallization set-up or other devices as long as the reaction conditions given below can be met.

It is known that organic impurities in the educts may form colored by-products in the course of the reaction and/or during purification of alkanesulfonic acids, e.g. during distillation of, for example, MSA.

As mentioned above, in some manufacturing processes for alkanesulfonic acids, an alkane (for example methane) is used as raw material. Potential sources for alkanes, like methane, are natural gas, biogas, side streams from industrial processes generated e.g. in cracker plants, liquefied natural gas etc. In all cases the alkane does not occur in pure form but contains other compounds, which compounds exactly depends on the source of the alkane, e.g. methane. In some processes alkanes can be used as mixture, in other cases the alkane, e.g. methane, needs to be used in a more or less pure form.

Often alkanes, like methane, are obtained from natural gas. For example in the case of methane, natural gas contains further components like higher homologues of methane such as ethane, propane or butane.

According to Ullmann's Enzyklopädie, "Natural Gas", vol. 23, p. 740, natural gas typically contains several hydrocarbons, for example methane in a molar fraction of 0.75 to 0.99, ethane in a molar fraction of 0.01 to 0.15 and propane in a molar fraction of 0.01 to 0.10, as well as several nonhydrocarbons, for example nitrogen in a typical molar fraction of 0.00 to 0.15.

In order to purify an alkane (e.g. methane) for industrial use, the natural gas is usually subjected to a pressure-swing adsorption (PSA) process. Depending on the design of the PSA process different degrees of purity of the alkane (e.g. methane) can be achieved.

For example in the methane used as educt for the reaction with SO3 in a process for manufacturing MSA, e.g. ethane, propane and higher alkanes generally occur as impurities. In the reaction of ethane and propane, ethanesulfonic acid and propanesulfonic acid and other side products could be formed, respectively. Higher alkanes yield e.g. sulfonated products. These undesired by-products may decompose during distillation due to the high temperatures in the column, thereby forming colored impurities, inter alia.

EP 1 591 563 A1 (Ishihara Chem. et al.) describes a tin-containing plating bath comprising, inter alia, at least one aliphatic sulfonic acid. It is mentioned that alkanesulfonic acids contain as impurities various sulfur-containing compounds; there is no disclosure of other impurities relating to alkanesulfonic acids with varying alkane chain length apart from the target chain length used for the production of alkanesulfonic acids (e.g. methanesulfonic acid).

U.S. Pat. No. 4,450,047 discloses a process for recovering anhydrous alkanesulfonic acids using falling film evaporation. Allegedly a purity of at least 99.5 weight percent is reached. In order to reduce the color number of the product, hydrogen peroxide is added to the final product.

EP 0 675 106 A1 describes a process for the preparation of alkane sulfonic acids with a high purity. Impurities, namely methylmethanethiosulfonate and dimethyldisulfide, are reduced by intensifying the mixing of the reactants methylmercaptane and chlorine in the active zone of the reactor. There is no mention of other side products.

U.S. Pat. No. 4,895,977 relates to the production of alkanesulfonic acids, using ozone to remove oxidizable organic purities in the product.

U.S. Pat. No. 5,583,253 describes a method of preparing purified alkanesulfonic acids, wherein chlorine is added to remove oxidizable impurities in the product.

Furthermore, JACS 1996, 118, p. 13111 et seq describes the radical-initiated functionalization of methane and ethane in fuming sulfuric acid but no information is given with regard to purity of the final product or its purification.

All these publications describe measures to optimize the synthesis sequence and to some extent the work-up focusing on the main reactants and their reactions products, e.g. methylmercaptane and chlorine, dimethyldisulfide and nitric acid. Furthermore, most conventional methods for manufacturing alkanesulfonic acids, for example MSA, resort to oxidizing agents, like hydrogen peroxide, in order to reduce the amount of organic impurities and/or decrease the color number of the final product.

None of these patents describe any measures how to obtain alkanesulfonic acids, in particular MSA, with a high purity when other impurities are involved which are not generated in the course of the reaction but are introduced e.g. via the raw materials. None of the mentioned documents disclose the use of especially pure educts, in particular pure methane with a defined degree of purity.

Thus, an additional process step and additional ingredients are required in the conventional art.

Ideally, the manufacturing process should be simple, cost efficient, energy saving, selective, should offer a high product yield, a low amount of byproducts and should use mild reaction conditions. Furthermore, ideally, a product with a low color number should result. Several efforts have been conducted to optimize the MSA production methods. However, for the manufacturing processes known in the art there is still a need to overcome associated disadvantages.

In the light of the prior art the technical problem underlying the present invention was the provision of a process for manufacturing of methane sulfonic acid (MSA) that overcomes the disadvantages of those processes known in the art.

In particular, a problem to be solved by the present invention was to provide a process for the manufacture of methanesulfonic acid in a higher yield and/or with a higher degree of purity. A higher degree of purity of the product may, inter alia, be demonstrated by a lower color number or the effort to be put into the purification. Thus, a further problem underlying the present invention was to provide a process for the manufacture of methanesulfonic acid with a lower color number. Another problem upon which the present invention is based is the provision of a process for manufacturing of methane sulfonic acid (MSA) which facilitates downstream distillation and/or purification steps, for example by reducing the energy input required for distillation and/or purification.

Surprisingly it was inter alia found that by using methane with a lower degree of impurities, in particular ethane and propane and C4-C8 alkanes, as educt, a process for the manufacture of methanesulfonic acid in a higher yield and/or with a higher degree of purity can be provided. Furthermore, a considerable decrease in the color number of the product was observed. This mentioned decrease in the color number of the product came as a surprise because a higher purity of educts fed into a chemical reaction process does not automatically result in a lower color number of the desired product.

SUMMARY OF THE INVENTION

The process of the present invention is simple and cost-efficient due to reduced energy consumption in the downstream purification steps (e.g. distillation) and the possibility to refrain from using additional decolorizing agents, e.g. oxidizing agents, and offers the possibility to achieve a high MSA yield and/or a highly pure MSA with low colorization.

The inventive process for manufacturing of methane sulfonic acid (MSA) thus overcomes at least some of the disadvantages known in the art.

The problem is solved by the features of the independent claims. Preferred embodiments of the present invention are provided by the dependent claims.

The invention therefore relates, in one aspect, to a process for the manufacturing of an alkanesulfonic acid by reaction (for example radical reaction, mainly or partially radical reaction) of an initiator composition with an alkane and sulfur trioxide comprising the steps:

i. Preparation of the initiator composition by reacting aqueous hydrogen peroxide with the components alkanesulfonic acid and/or $H_2SO_4$, ii. Reaction of initiator composition from step i. with sulfur trioxide and alkane to form an alkanesulfonic acid, for example by partially, mainly or completely radical reaction, Wherein alkane with a purity of at least 98.0 mol-% is used.

In the inventive process, step ii. may comprise or consist of a radical reaction. Step ii. may partially or mainly run according to a radical mechanism.

In the inventive process, methane with a purity of at least 98.0 mol-% is used.

In a preferred embodiment of the inventive process, methane with a purity of at least 98.5 mol-% is used.

In a further preferred embodiment of the inventive process, methane with a purity of at least 99.0 mol-% or 99.5 mol-% or even 99.7 or 99.8 or 99.9 mol-% is used.

In an embodiment of the inventive process, methane with a content of higher homologues of methane (including ethane, propane, butane and C5-C8 alkanes) of not more than 2.0 mol-% is used.

In an embodiment of the inventive process, methane with a content of ethane of not more than 1.5 mol-% is used. In a preferred embodiment this methane contains not more than 1.0 or 0.5 or 0.1 mol-% of ethane. Even more preferred is an ethane content of less than 0.05 or 0.01 mol-%. In an embodiment of the inventive process, methane with a content of propane of not more than 1.0 mol-% is used. In a preferred embodiment this methane contains not more than 0.5 or 0.1 mol-% of propane. Even more preferred is a propane content of less than 0.05 or 0.01 mol-% or 0.005 mol-%.

In an embodiment of the inventive process, methane with a content of butanes (total of n- and iso butane) of not more than 1.0 mol-% is used. In a preferred embodiment this methane contains not more than 0.5 or 0.1 mol-% of butanes. Even more preferred is a butane content of less than 0.05 or 0.01 mol-% or 0.005 mol-%.

The same limits as for butanes apply for the higher alkanes C5-C8.

The methane used for the inventive process generally has a maximum content of hydrocarbons of 500 ppm, preferably less than 400 ppm, less than 350 ppm, less than 300 ppm and more preferably less than 250 ppm or 200 ppm. The term "hydrocarbon" in the present invention comprises e.g. those hydrocarbons which are quoted in Ullmann's Enzyklopädie, "Natural Gas" (details see above), namely e.g. ethane, propane, n-butane, i-butane etc. The term hydrocarbon could furthermore comprise other, higher saturated and unsaturated, branched and non-branched hydrocarbons as e.g. ethylene, propylene, i-butylene etc.

The methane used for the inventive process generally has a maximum content of ethane of 300 ppm, preferably less than 200 ppm, more preferably less than 150 ppm.

Furthermore, the methane used for the inventive process generally has a maximum content of propane of 200 ppm, preferably less than 150 ppm, preferably less than 100 ppm, more preferably less than 80 ppm.

Furthermore, the methane used for the inventive process generally has a maximum content of butanes of 150 ppm, preferably less than 100 ppm, preferably less than 80 ppm, more preferably less than 50 ppm.

Furthermore, the methane used for the inventive process generally has a maximum content of higher alkanes C5-C8 of 100 ppm, preferably less than 80 ppm, more preferably less than 50 ppm.

The standard method to determine composition and purity of methane is gas chromatography.

The contents of the compounds mentioned above (e.g. ethane, propane, butanes and C5-C8 alkanes, further $H_2S$ and carbon dioxide) may thus be measured by gas chromatography.

The inventive process results in a product with a high purity.

In one embodiment of the inventive process, after step iii. MSA with a purity of greater than 98.0% by weight is obtained. Preferably, the inventive process yields MSA with a purity of greater than 99.0% by weight, more preferably greater than 99.5% or 99.8% by weight.

Furthermore, the inventive process surprisingly provides a product with a low color number. None of the patents/patent applications dealing with the reaction of methane and SO3 points out any issues related to the color number of the MSA produced. The more surprised were the authors of this patent application to observe colorization of the MSA produced according to descriptions of the state of the art. Choosing different recipes with varying reaction conditions with regard to pressure, temperature and molar ratios of the reactants allowed to increase or decrease the content of side products in the MSA produced, e.g. of MSA anhydride, methylmethanesulfonic acid or methylbisulfate, but did not yield any improvement with regard to colorization of the MSA.

In one embodiment of the inventive process, after the synthesis step ii. MSA yields of at least 80 mol-% are obtained. Preferably, the inventive process provides MSA yields above 83 mol-%. Even more preferably the process generates MSA yields higher than 85 mol-%, higher than 88 mol-% or 90 mol-%. In a further preferred embodiment, the inventive process generates MSA yields of higher than 93 mol-%, higher than 95 mol-% or even higher than 98 mol-%.

After painstaking investigations, the authors identified certain impurities as root cause of the colorization and developed countermeasures to reduce the degree of colorization of the raw MSA.

A typical and general process layout includes the following steps:
i. Synthesis of a starter, for example radical starter
ii. Synthesis of MSA
iii. Purification of MSA In one embodiment of the inventive process, MSA with an HAZEN color number of <400 HAZEN is obtained. In another embodiment MSA with an HAZEN color number of <300 HAZEN or 250 HAZEN is obtained. Preferably, the inventive process yields MSA with an HAZEN color number of <200, more preferably <150 or <100 or even <50 or <10 HAZEN.

The color number is measured, unless mentioned otherwise, according to a standard procedure given in the literature, i.e. DIN EN ISO 6271 (platinum cobalt scale).

It is to be noted that the mentioned low color number is obtained from the inventive process without further process steps (except, optionally, distillation and/or crystallization). To be more precise, in the inventive process it is not necessary to add oxidizing compounds and/or bleaching agents at the end of the process, contrary to the disclosures of the prior art.

The synthesis of a raw MSA may for example be done in the following way:
a) Generating a starter solution (initiator solution, for example radical starter solution), for example by adding H2O2 to a solution containing MSA and/or Oleum and/or sulfuric acid and/or MSAA.
b) Inerting the whole system e.g. with N2 or by evacuating the system and refilling it with N2 and executing this procedure once or several times (optionally after step c))
c) Charging a reactor with the initiator solution and optionally additional MSA, H2SO4, Oleum, SO3 or mixtures thereof basically free of water
d) Charging the same reactor with methane
e) Set the pressure to >25 bar (30-150 bar, 50-100 bar)
f) Set the temperature to >30° C. (30-70° C., 45-65° C.) (or alternatively exchange steps e) and f))
g) In a continuous mode of operation continuously remove the reaction product from the reactor and constantly replenish the reactor with methane, SO3 and starter solution (e.g. radical starter solution) to keep concentrations in the reactor constant (steady state).

Other options to carry out the synthesis can be found e.g. in WO 2015/071365 or in WO 2004/041399.

In an embodiment of the invention the starter (e.g. a radical starter) can be formed in situ as part of step ii, e.g. by addition of H2O2 solution to the reactor itself or by addition into one of the pipelines feeding other liquid streams into the reactor.

In a preferred embodiment the initiator composition in step a) further comprises sulfur trioxide.

In a preferred embodiment the initiator composition in step a) further comprises a recycle stream from the bottom purge of the distillation of methanesulfonic acid mainly consisting of methane sulfonic acid and sulfuric acid.

In a preferred embodiment the reaction (e.g. radical reaction) described in steps c)-f) comprises an initiation reaction and a propagation reaction.

In a preferred embodiment the process comprises a step iii. for purification of methane sulfonic acid and optionally methane sulfonic acid anhydride obtained from the synthesis described in steps a)-g) or from alternative procedures described in the literature (e.g. WO 2015/071365 or WO 2004/041399).

In a preferred embodiment the purification step iii. is a single step distillation or a multi step distillation.

In an embodiment of the inventive process, the purification step iii. comprises at least two distillation steps.

In an embodiment of the inventive process, the purification step iii. comprises a first distillation step at a temperature in the range of 30° to 220° C., preferably 100° to 200° C. and a subsequent second distillation step at a temperature in the range of 150° to 220° C., preferably 160° to 200° C. The temperatures given are the temperatures at the bottom of the respective distillation columns.

In an embodiment of the inventive process, the purification step iii. comprises a first distillation step at a pressure in the range of 5 to 1000 mbar, preferably 7 to 200 mbar and a subsequent second distillation step at a pressure in the range of 0.1 to 20 mbar, preferably 2 to 10 mbar. In an embodiment of the inventive process, the purification step iii. is performed in at least two separate distillation columns, preferably in two or three separate distillation columns.

In an embodiment of the invention, between step ii. and step iii. a step can be introduced to release the pressure used in step ii. before entering the purification step iii., e.g. a distillation. Such a step ("flash" or "flash unit") could be carried out in one or a sequence of normal vessels, in one or a sequence of pressure control valves with pressure release option, in one or a sequence of flash drums or any other set-up suitable for the purpose of pressure release from step ii. to step iii. A flash unit furthermore supports the removal of light boilers like unreacted methane from the product stream leaving step ii. prior to entering step iii. Thus, the purification step iii. has to handle lower amounts of light boilers than without a flash. These lights could be incinerated to generate heat or recycled into the process or used for other purposes. Reduction of the pressure between steps ii. and iii. in a flash is preferred.

In an embodiment of the inventive process, in a first distillation step at a temperature of 30° to 220° C. (preferably 100° to 200° C., more preferably 120° to 190° C.) and a pressure of 5 to 1000 mbar (preferably 7 to 200 mbar, more preferably 10 to 100 or 10 to 50 mbar), a large percentage of the methane and sulfur trioxide contained in the reaction mixture is removed, e.g. more than 80%, preferably more than 90% or 95% or even more than 98%. In a second distillation step at a temperature of 150° C. to 220° C. (preferably 160° C. to 200° C.) and a pressure of 0.1 to 20 mbar (preferably 2 to 10 mbar), mainly MSA and sulfuric acid are separated. MSA can be withdrawn at the head or the side discharge of the column, whereas e.g. sulfuric acid and methanedisulfonic acid remain in the sump.

In another embodiment of the invention, at least a part of the bottom fraction of the MSA distillation in column 1 and/or in column 2 and/or additional downstream columns is not purged from the system but at least partially recycled to the synthesis step of the starter solution (e.g. radical starter solution) or to the synthesis step of the MSA synthesis with $CH_4$ and $SO_3$.

In a preferred embodiment of the inventive process, the two-stage distillation process is performed in at least two separate distillation columns or alternative equipment meeting the same functionality, e.g. perform the first distillation step in a simple vessel under the conditions given above. This is preferable inter alia because a preferred embodiment of the inventive process for the synthesis of MSA is a continuous process.

In an embodiment of the inventive process, said distillation process comprising at least two distillation steps involves stripping of the distillation mixture with an inert gas in the first distillation stage, selected from the list consisting of nitrogen and argon.

In an embodiment of the inventive process, the alkanesulfonic acid is withdrawn at the side discharge of the distillation column in the second distillation stage and also of the columns of potential further columns.

In an embodiment of the inventive process, the process is a continuous process.

In a preferred embodiment the purification step iii. for purification of MSA, and optionally MSA anhydride, obtained e.g. from steps a)-g) is a crystallization followed by a solid-liquid separation.

In a preferred embodiment step i. is conducted in a reactor A, step ii. is conducted in a reactor B and step iii. is conducted in a column or set of columns C, and whereas reactor A, reactor B and column C are connected to conduct the process for the manufacturing of methane sulfonic acid continuously.

In a preferred embodiment step iii. is conducted in a crystallization unit, where the mother liquor is recycled into the crystallization unit or into the reactor A or into the reactor B or drained.

In a preferred embodiment an additional step iv., after methane sulfonic acid is obtained from step ii., methane sulfonic acid anhydride is provided for subsequent charging of reactor A with methane sulfonic acid anhydride.

In a preferred embodiment the provision of methane sulfonic acid anhydride in step iv. for subsequent charging of reactor A, comprises a separated methane sulfonic acid anhydride manufacturing step after step iii. or a separation of methane sulfonic acid anhydride as side-component from step iii.

In a preferred embodiment after step i., after the initiator composition is formed, the water content is in the range from 0 wt-% to 1 wt-% and the content of sulfuric acid is in the range from 0 wt-% and 20 wt-% or in the range from 0 wt-% and 15 wt-%, 0 wt-% and 10 wt-%, 0 wt-% and 5 wt-% or 0 wt-% and 2 wt-%.

In a preferred embodiment after step ii., after methane sulfonic acid is formed, the content of sulfuric acid is in the range from 0 wt-% to 50 wt-%, or 0 wt-% to 40 wt-%, or 0 wt-% to 30 wt-%, or 0 wt-% to 20 wt-%, or 0 wt-% to 15 wt-%, or 0 wt-% to 10 wt-%, or 0 wt-% to 5 wt-%.

In a preferred embodiment after step iii., after methane sulfonic acid is purified, the content of sulfuric acid is in the range from 0 ppm to 200 ppm, preferred 0 ppm to 100 ppm and most preferred 0 ppm to 50 ppm.

In a preferred embodiment the temperature in step i. is in the range from −5° C. to 25° C., the temperature is step ii. is in the range from 25° C. and 80° C., and the temperature in step iii. in the bottom of the column is in the range from 30° C. to 220° C.

In a preferred embodiment the pressure in step i. is about 1013 mbar or beyond 1013 mbar, the pressure in step ii. is in the range from 10 bar to 150 bar, and the pressure in step iii. is in the range from 2 mbar to 1000 mbar.

In an embodiment MSA anhydride is used as water scavenger, whereas methane sulfonic acid is manufactured preferably by radical reaction (or at least partially radical reaction), and whereas an initiator composition comprises aqueous hydrogen peroxide, methane sulfonic acid, optionally sulfur trioxide and sulfuric acid and methane sulfonic acid anhydride.

One embodiment of the invention comprises the use of an initiator composition comprising methane sulfonic acid, methane sulfonic acid anhydride and aqueous hydrogen peroxide for the manufacturing of methane sulfonic acid, preferably by radical reaction (or at least partially radical reaction).

In an embodiment of the invention, an initiator composition is used, whereas the initiator composition additionally comprises sulfuric acid and/or sulfur trioxide.

The invention further relates to MSA, whereas after purification in step iii. the methane sulfonic acid content is in the range from 99.5 wt-% to 100 wt-%.

Further objects of the present invention include methansulfonic acid, obtainable by the inventive process, and the use of a methanesulfonic acid, obtainable by the inventive process, e.g. for cleaning applications or in an electroplating process or as acidic catalyst e.g. in esterification reactions.

BRIEF DESCRIPTION OF THE FIGURES

FIG. 1 shows is an exemplary, schematic diagram of an embodiment of the process of the present invention.

FIG. 2 shows the reaction parameters according to example 1.

FIG. 3 shows the reaction parameters according to example 2.

FIG. 4 shows the reaction parameters according to example 3.

DETAILED DESCRIPTION OF THE INVENTION

In a first aspect the invention relates to a process for manufacturing of methane sulfonic acid (MSA) by reaction (for example radical reaction) of an initiator composition with methane and sulfur trioxide comprising the steps:
i. Preparation of the initiator composition by mixing aqueous hydrogen peroxide ($H_2O_2$) with the components methane sulfonic acid (MSA), optionally sulfur trioxide ($SO_3$) and optionally sulfuric acid (H2SO4) and optionally methane sulfonic acid anhydride (MSA anhydride or MSAA),
ii. Reaction of the initiator composition from step i. with sulfur trioxide and methane to form MSA (preferably by radical reaction), wherein methane with a purity of at least 98 mol-% is used.

It was found that reduction of the percentage of hydrocarbons as listed above (see ranges quoted from Ullmann's Enzyklopädie), e.g. ethane and/or propane and/or butanes and/or C5-C8 alkanes in the methane used as educt had positive effects both on the product (yield, purity, colour number) and the manufacturing process (lower energy consumption).

In a preferred embodiment of the inventive process, methane with a purity of at least 98.0 mol-% is used.

In a further preferred embodiment of the inventive process, methane with a purity of at least 98.5 mol-% or 99.0 mol-% or 99.5 mol-% or even 99.7 or 99.8 or 99.9 mol-% is used.

It was also found that in an embodiment of the invention a combination of the components in step i. is suitable to form radicals as initiators for a subsequent radical reaction in combination with sulfur trioxide and methane. In step i. particularly the components aqueous hydrogen peroxide, methane sulfonic acid, optionally sulfur trioxide ($SO_3$) and sulfuric acid and methane sulfonic acid anhydride are charged together in a reactor. Preferably, step i. comprises the substeps i1) and i2). In sub-step i1) for example the components aqueous hydrogen peroxide ($H_2O_2$), methane sulfonic acid (MSA) and sulfuric acid and methane sulfonic acid anhydride (MSA anhydride) are mixed together. In step i1) for example water is removed and anhydrous conditions are generated, in particular due to MSA anhydride. In sub-step ii2) for example sulfur trioxide ($SO_3$) is added.

As process conditions for preparing the initiator composition the following parameters are preferably selected in step a)
- temperature preferably in the range from −5° C. to +25° C., and
- pressure preferably in the range from 0.5 bar to 10 bar, preferably in the range from 0.8 bar to 5 bar, most preferably close to normal pressure of approximately 1 bar (about 1013 mbar).

The amount of MSA anhydride added to the initiator composition (starter solution) in step a) is equivalent (calculated as mol, not as gram (g)) to the amount of water introduced with the $H_2O_2$ solution. It is for example to note that the $H_2O_2$ solution, the MSA anhydride, MSA, optionally sulfuric acid and optionally the recycle stream from the MSA distillation are combined first. In particular, sulfur trioxide ($SO_3$) is introduced only after all free water has reacted with the MSA anhydride.

Optionally, the initiator composition in step i. further comprises sulfur trioxide ($SO_3$). A further option for the initiator composition in step i. is a recycle stream from the bottom purge of the distillation of MSA comprising mainly MSA and $H_2SO_4$. In step i. of an embodiment of the invention an initiation mixture is prepared, which is suitable to form radicals at elevated temperature conditions or under photochemical initiation. The formation of radicals then takes place in a so-called initiation reaction. The radicals are particularly formed in the presence of methane and/or sulfur trioxide for example as part of step ii. Step i. yields a mixture comprising one or more of the components peroxo-monosulfuric acid (Caro's acid), peroxo-disulfuric acid (Marshall's acid), mono(methyl-sulfonyl)peroxide (MMSP) and/or di(methyl-sulfonyl)peroxide (DMSP), and besides, optionally, MSA and/or H2SO4. These components may act as intermediates, which further form in particular methyl radicals and/or methane sulfonic acid radicals in the synthesis of MSA according to an embodiment of step ii. Preferably, the radical reaction in an embodiment of step ii. comprises an initiation reaction and a propagation reaction.

The formation of radicals in an embodiment of the present invention in particular takes place in a separate step ii. wherein the initiator composition from step i. is brought in contact with methane and sulfur trioxide (initiation reaction). In a subsequent reaction (propagation reaction) which is preferably also part of an embodiment of step ii. then the formation of MSA takes place by reacting the initiator composition in a reaction with methane and sulfur trioxide, for example by radical reaction or at least partially a radical reaction.

In an embodiment of the present inventive process, in step ii. the temperature-induced at least partially radical formation starts the radical chain reaction leading to the formation of methanesulfonic acid:

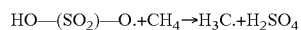
$HO-(SO_2)-O.+CH_4 \rightarrow H_3C.+H_2SO_4$

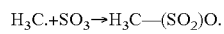
$H_3C.+SO_3 \rightarrow H_3C-(SO_2)O.$

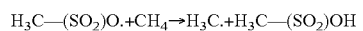
$H_3C-(SO_2)O.+CH_4 \rightarrow H_3C.+H_3C-(SO_2)OH$

In another embodiment of this invention the present inventive process comprises at least partially other reaction pathways than solely a radical pathway, e.g. ionic pathways or combinations of radical and ionic pathways.

Optionally, purification step iii. may be carried out in more than two purification actions in order to further purify the MSA from step ii. and to further decrease e.g. the $H_2SO_4$ content in the purified MSA from step iii. A purification step is for example a distillation or crystallization.

Preferably, the process of this invention comprises a step iii. for purification of MSA obtained from step ii. It is further preferred that the purification step iii. is a single step distillation or a multi-step distillation.

It is further preferred that the purification step iii. is a crystallization and/or a solid-liquid separation. In an embodiment of the invention the purification step iii. is a combination of a crystallization and/or a solid-liquid separation with a distillation.

It is preferred that step i. is conducted in a reactor A, step ii. is conducted in a reactor B or a sequence of reactors and step iii. is conducted in a column or in a set of columns C, and whereas the reactor A, reactor(s) B and column(s) C are connected to conduct the process for the manufacturing of MSA continuously. If step iii. is carried out in a multi-step distillation at least the first purification step can be carried out in a simple vessel which can be stripped with a carrier gas or operated under vacuum as indicated below. Stripping by addition of a gaseous carrier is being regarded as a distillative or evaporative process.

Optionally, in an additional step iv., after MSA is obtained from step ii. or iii. respectively, MSA anhydride is provided for subsequent charging of reactor A with MSA anhydride.

Optionally, step iv. for providing MSA anhydride for subsequent charging of reactor A comprises a separated MSA anhydride manufacturing step after step iii. or MSA anhydride is provided for subsequent charging of reactor A by separation of MSA anhydride as side-product from step iii.

Preferably, prior to starting the synthesis/reaction sequence, the equipment used for steps i. to iv. is set under inert conditions, e.g. by rinsing with inert gases as nitrogen or argon, by repeated evacuation of the system and refilling the system with inter gases or by other means yielding the same effect. In particular, step i. and ii. should be carried out under inert conditions.

Preferably, the temperature in step i. is in the range from −5° C. to +25° C., more preferably in the range from −2° C. to +15° C. and most preferably in the range from 0° C. to 10° C., or any value between these values or ranges thereof. Preferably, the temperature in step ii. is in the range from 25° C. to 80° C., more preferably in the range from 30° C. to 70° C. and most preferably in the range from 40° C. to 60° C., or any value between these values or ranges thereof. Preferably, the temperature at the bottom of the column in step iii. is in the range from 30° C. to 220° C., more preferably in the range from 100° C. to 200° C., or any value between these values or ranges thereof. If the distillation in step iii. is carried out in two or more steps, the first step can be operated for example at temperatures in the range from 30° C. to 220° C., preferably in the range from 100° C. to 200° C., and more preferably in the range from 120° C. to 190° C., or any value between these values or ranges thereof. Alternatively, if more than one column is used, the set of columns are all operated in the range from 30° C. to 220° C. or 100° C. to 200° C. or 120° C. to 190° C. at the bottom.

Preferably, the pressure in step i. can be any pressure, preferably a pressure close to normal conditions or for example slightly increased pressures, in particular in the range from 0.5 bar to 10 bar, more preferably in the range from 0.8 bar to 5 bar and most preferably at about 1013 mbar or for example at slightly elevated pressure beyond 1013 mbar, e.g. 2 bar (absolute), or any value between these values or ranges thereof. The pressure in step ii. is preferably in the range from 10 bar to 150 bar, more preferably in the range from 20 bar to 100 bar, and most preferably in the range from 40 bar to 80 bar, or any value between these values or ranges thereof. The pressure in step iii. is preferably in the range from 2 mbar to 1000 mbar, more preferred in the range from 5 to 300 mbar, or any value between these values or ranges thereof. In an embodiment of this invention a flash or a series of flash installations is introduced between steps ii. and iii. to allow for single or stepwise adaptation from the pressure applied in step ii. to the pressure in step iii. and to reduce the amount of light boilers carried over from step ii. into step iii. If the distillation in step iii. is carried out in two or more steps, the first step can be operated at pressures in the range from 5 mbar to 1000 mbar, preferably in the range from 7 mbar to 200 mbar, and most preferably in the range from 10 mbar to 100 mbar or 10 mbar to 50 mbar, or any value between these values or ranges thereof. The second step can be carried out at a pressure between 0.1 and 20 mbar, preferably between 2 and 10 mbar. Alternatively, if more than one column is used, the set of columns are all operated in the range from 0.1 to 20 bar, preferably between 2 to 10 bar.

A further aspect of the invention relates to the use of an initiator composition comprising MSA, optionally sulfuric acid, optionally $SO_3$ and/or a recycle stream from the bottom purge of the distillation of MSA comprising mainly MSA and $H_2SO_4$, MSA anhydride and aqueous $H_2O_2$ for the manufacturing of MSA, preferably by radical reaction (or partially radical reaction).

A further aspect of the invention relates to methane sulfonic acid (MSA), whereas after purification in step iii. the MSA content is above 98 wt-%, preferably in the range from 99.0 wt-% to 100 wt-% or from 99.5 wt-% to 100 wt-%, or any value between these values or ranges thereof. It is in particular preferred that after purification in step iii. the MSA content is about 99.6 wt-%, 99.7 wt-%, 99.8 wt-% or 99.9 wt-%. It is further preferred that after purification in step iii. the $H_2SO_4$ content is preferably about 200 ppm or lower, more preferably about 150 ppm or lower, even more preferably about 100 ppm or lower, and most preferably about 50 ppm or lower, or any value between these values or ranges thereof. It is in particular preferred that after purification in step iii. the sulfuric acid content is in the range from 0 ppm to 20 ppm, preferably in the range from 0 ppm to 15 ppm, more preferably in the range from 0 ppm to 10 ppm and most preferably in the range from 0 ppm to 5 ppm, or any value between these values or ranges thereof.

The same target values for the purified MSA after step iii. apply if purification is done via a crystallization step or a combination of distillation and crystallization.

If using a dedicated pressure swing adsorption unit to provide purified methane according to the invention, use the "waste methane" at the outlet of the pressure swing adsorption, which is enriched in ethane, propane, butanes and higher alkanes, alkenes or alkines as fuel to heat the MSA distillation sump via indirect heating, e.g. generate steam and use as heat carrier for a heat exchanger or heat oil as heat carrier for a heat exchanger.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferable within 10%, and more preferably within 5% of a given value or range. The term "about" or "approximately" as used herein also includes the exact respective values or ranges.

Throughout the specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude material or steps that do not materially affect the basic and novel characteristics of the claim.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

EXAMPLES

Synthesis of Methanesulfonic Acid by Sulfonation of Methane—General Procedure

Sulfonation of methane was carried out in a 300 mL autoclave (material of construction HC-4) which is equipped with a glass liner, baffles (HC-4), a thermo-sleeve (HC-4) and a magnetic stirring bar (magnetic metal core with PTFE lining). Handling of sulfur trioxide and sulfur trioxide containing solutions (e.g. oleum) is carried out under inert conditions ($N_2$ or Ar atmosphere) to avoid $SO_3$-losses by formation of sulfuric acid.

In a typical experiment, a 250 mL round bottom flask is charged with a sulfur trioxide containing solution (e.g. oleum with 32 wt. % sulfur trioxide). Thereafter, the solution is cooled down to a temperature of 10-20° C. Subsequently, an aqueous $H_2O_2$ solution (e.g. 70 wt. %) is added slowly via immersed tube into the liquid under stirring. The mixture is transferred to the autoclave and the autoclave is quickly closed. After closing, the head space is repeatedly flushed with $N_2$ to render the autoclave inert. After a pressure of 50-100 bar methane has been set, the temperature is slowly raised to 40-60° C. at a rate of 0.4-0.6° C./min causing an additional pressure increase. Examples of typical curves of pressure and temperature over the duration of the experiment are given in FIGS. 2-4. (A typical reactor set-up for an embodiment of the invention is shown in FIG. 1).

In the course of several hours the pressure drops by up to ca. 50 bar and plateaus. The residual pressure is released slowly and the liquid is recovered as crude product. The color ranges from pale-yellow to dark red depending on the quality of employed methane gas.

In order to show the range of typical side products, in some examples the crude product is characterized by $^1$H- and $^{13}$C-NMR spectroscopy ($C_6D_6$ was used in a capillary as the lock reference; device: Bruker Avance III HD 400 MHz; identification of main product and side products) Moreover all product mixes with significant methane conversion (indicated by the pressure drop) were characterized by acidimetry (crude product is diluted with $H_2O$, determination of MSA- and $H_2SO_4$ content in wt. %), and measurement of the color index (Hazen scale; apparatus: LICO 500, Hach/Lang, upward limit 1000 Hazen).

The examples are meant to further explain effects related to the reaction of CH4 and SO3 in the synthesis step ii. The formation of the starter (step i.) is described as part of the overall synthesis sequence in one embodiment of the invention.

The calculation of MSA yields in the following examples considers only what happens in the synthesis reactor (unless explicitly noted otherwise).

The calculation of MSA yields is done as follows (unless otherwise mentioned).

Y(MSA based on SO3, given in %)=((MSA at the end of the reaction in mol)/(SO3 available for the reaction with CH4 in mol))×100

MSA at the end of the reaction is determined by weighing the content of the reactor after reaction, determining the MSA concentration by acidimetry in wt-%, multiplying these two values and converting them into mol MSA (output given in mol MSA formed during reaction and the mol SO3 converted to MSA are equivalent).

SO3 available for the reaction with CH4 is determined by the total weight of oleum introduced into the reactor—and thus the total amount of SO3—corrected by the amount of water in mol introduced via the H2O2 solution during formation of the starter which captures SO3 and forms H2SO4 (output given in mol).

Employed primary methane sources ($CH_4$ 99.5% and $CH_4$ 99.995%) are analyzed by gas chromatography. Ethane and propane are commercially available. Impurities in these gases are specified. Gases 4 and 7 were premixed. The compositions of the used gas mixtures are given in Table 1. (Methane pre PSA and post PSA are available commercially in gas bottles.)

TABLE 1

Gas composition of used gases

| | methane (vol %) | ethane (vol %) | propane (vol %) | other hydrocarbons (vol %) | nitrogen (vol %) | carbon dioxide (vol %) |
|---|---|---|---|---|---|---|
| 1 | 99.995 | <2 ppm | <2 ppm | <10 ppm | | |
| 2 | 99.649 | 225-227 ppm | <2 ppm | 22 ppm | | |
| 3 | 99.500 | 322-324 ppm | <2 ppm | 31-32 ppm | | |
| 4 | 97.939 | 0.906 | 0.251 | | 0.794 | 0.110 |
| 5 | 97.507 | 0.446 | 0.124 | | 1.869 | 0.054 |
| 6 | 99.409 | 0.227 | 0.063 | | 0.265 | 0.037 |
| 7 | 98.700 | 0.010 | 0.005 | | 1.270 | |
| 8 | 96.995 | 2.999 | | <21 ppm | | |
| 9 | 96.995 | | 2.999 | <22 ppm | | |
| 10 | <25 ppm | 99.950 | | <375 ppm | <40 ppm | <5 ppm |
| 11 | | | 99.950 | <400 ppm | <40 ppm | <5 ppm |

TABLE 2

Overview over yield and color index.

| Example No. | Gas composition | Yield (%) | Color index (HAZEN) |
|---|---|---|---|
| 1 | 1 | 90 ± 2 | 58 |
| 2 | 2 | 85 ± 2 | 102 |
| 3 | 3 | 90 ± 2 | 118 |
| 4 | 4 | 5 ± 2 | out of scale |
| 5 | 5 | 31 ± 2 | out of scale |
| 6 | 6 | 86 ± 2 | 85 |
| 7 | 7 | 94 ± 2 | n.a. |
| 8 | 8 | — | out of scale |
| 9 | 9 | — | out of scale |

Example 1

Sulfonation of methane was carried out according to the procedure described afore. 0.20 mL $H_2O_2$ (aqueous solution, 70 wt. % $H_2O_2$) were added to 103.06 g oleum (32 wt. % $SO_3$) under cooling to 11-12° C. and stirring. 93.09 g of the mixture were transferred into the autoclave. After rendering inert, a methane pressure of 100 bar was set. The purity of the employed methane gas was 99.995% (gas composition 1, cf. Table 1). Setting the temperature to 50° C. (at a rate of 0.4° C./min), the pressure increased to approx. 110 bar. After 5 h the pressure dropped by 26 bar. 97.25 g of a non-fuming pale-yellow liquid was recovered from the autoclave. A color index of 58 Hazen was measured. The methanesulfonic acid content was determined to be 31.8 wt. % corresponding to a yield of 90±2%. Via NMR the following side products could be identified: 0.01 wt. % $H_3C$—($SO_2$)—$OCH_3$ (methyl methanesulfonate), 0.07 wt. % $H_3CO$—($SO_2$)—OH (methyl bisulfate), traces of HO—($SO_2$)—$CH_2$—($SO_2$)—OH (methanedisulfonic acid).

Results are shown in FIG. 2.

Example 2

Sulfonation of methane was carried out according to the procedure described afore. 0.34 mL $H_2O_2$ (aqueous solution, 70 wt. % $H_2O_2$) were added to 101.27 g oleum (32 wt. % $SO_3$) under cooling to 12-16° C. and stirring. 85.91 g of the mixture were transferred into the autoclave. After rendering inert, a pressure of 30 bar of gas 3 and 70 bar of gas 1 was applied for a total pressure of 100 bar. The composition of the employed gas is given in Table 1 (gas composition 2). Setting the temperature to 50° C. (at a rate of 0.5° C./min), the pressure increased to approx. 111 bar. After 3 h the pressure dropped by 20 bar. 89.53 g of a non-fuming yellowish liquid was recovered from the autoclave. The methanesulfonic acid content was determined as 29.2 wt. % referring to a yield of 85±2%. A color index of 102 Hazen was obtained. Via NMR the following side products could be identified: 0.03 wt. % $H_3C$—($SO_2$)—$OCH_3$ (methyl methanesulfonate), 0.18 wt. % $H_3CO$—($SO_2$)—OH (methyl bisulfate), 0.02 wt. %, HO—($SO_2$)—$CH_2$—$CH_2$—O—($SO_2$)—OH, <0.01 wt. % $H_3C$—$CH_2$—($SO_2$)—OH (ethanesulfonic acid), traces of HO—($SO_2$)—$CH_2$—($SO_2$)—OH (methanedisulfonic acid) and HO—($SO_2$)—$CH_2$—$CH_2$—($SO_2$)—OH (ethanedisulfonic acid).

Results are shown in FIG. 3.

Example 3

Sulfonation of methane was carried out according to the procedure described afore. 0.34 mL $H_2O_2$ (aqueous solution, 70 wt. % $H_2O_2$) were added to 100.93 g oleum (32 wt. % $SO_3$) under cooling and stirring. 88.28 g of the mixture were transferred into the autoclave. After rendering inert, a methane pressure of 100 bar was set. The purity of the employed methane gas was 99.5% (gas composition 3, cf. Table 1). Setting the temperature to 50° C. (at a rate of 0.6° C./min), the pressure increased to approx. 111 bar. After 4 h the pressure dropped by 26 bar. 92.27 g of a non-fuming yellow liquid was recovered from the autoclave. The methanesulfonic acid content was determined as 30.8 wt. % referring to a yield of 90±2%. A color index of 110 Hazen was obtained. Via NMR the following side products could be identified: 0.02 wt. % $H_3C$—($SO_2$)—$OCH_3$ (methyl methanesulfonate), 0.17 wt. % $H_3CO$—($SO_2$)—OH (methyl bisulfate), 0.03 wt. %, HO—($SO_2$)—$CH_2$—$CH_2$—O—($SO_2$)—OH, 0.01 wt. % $H_3C$—$CH_2$—($SO_2$)—OH (ethanesulfonic acid), traces of HO—($SO_2$)—$CH_2$—($SO_2$)—OH (methanedisulfonic acid) and HO—($SO_2$)—$CH_2$—$CH_2$—($SO_2$)—OH (ethanedisulfonic acid).

Results are shown in FIG. 4.

Example 4—Comparative

Sulfonation of methane was carried out according to the procedure described afore. 0.34 mL $H_2O_2$ (aqueous solution, 70 wt. % $H_2O_2$) were added to 98.93 g oleum (32 wt. % $SO_3$) under cooling to 12-16° C. and stirring. 86.53 g of the mixture were transferred into the autoclave. After rendering inert, a methane pressure of 100 bar was set. The purity of the employed methane gas is given in Table 1 (gas composition 4). Setting the temperature to 50° C. (at a rate of 0.5° C./min), the pressure increased to approx. 110 bar. After 19 h the pressure dropped by about 18 bar. 85.29 g of a fuming redish liquid was recovered from the autoclave. The methanesulfonic acid content was determined as 1.4 wt. % referring to a yield of 5±2%. A color index in Hazen could not be obtained as the solution was out of HAZEN scale.

Example 5—Comparative

Sulfonation of methane was carried out according to the procedure described afore. 0.34 mL $H_2O_2$ (aqueous solution, 70 wt. % $H_2O_2$) were added to 101.28 g oleum (32 wt. % $SO_3$) under cooling to 12-16° C. and stirring. 90.48 g of the mixture were transferred into the autoclave. After rendering inert, a nitrogen pressure of 1 bar remained. A pressure of 50 bar of gas 4 and 50 bar of gas 1 was applied for a total pressure of 101 bar. The composition of the employed gas mixture is given in Table 1 (gas composition 5). Setting the temperature to 50° C. (at a rate of 0.5° C./min), the pressure increased to approx. 111 bar. After 19 h the pressure dropped by about 5 bar. 89.54 g of a fuming reddish liquid was recovered from the autoclave. The methanesulfonic acid content was determined as 11.2 wt. % referring to a yield of 31±2%. A color index in Hazen could not be obtained as the solution was out of HAZEN scale.

Example 6

Sulfonation of methane was carried out according to the procedure described afore. 0.34 mL $H_2O_2$ (aqueous solution, 70 wt. % $H_2O_2$) were added to 100.39 g oleum (32 wt. % $SO_3$) under cooling to 12-16° C. and stirring. 85.34 g of the mixture were transferred into the autoclave. After rendering inert, a pressure of 25 bar of gas 4 and 75 bar of gas 1 was applied for a total pressure of 100 bar. The composition of the employed gas mixture is given in Table 1 (gas composition 6). Setting the temperature to 50° C. (at a rate of 0.5° C./min), the pressure increased to approx. 112 bar. After 46 h the pressure dropped significantly. 88.57 g of a non-fuming slightly yellow liquid was recovered from the autoclave. The methanesulfonic acid content was determined as 29.8 wt. % referring to a yield of 86±2%. A color index of 85 Hazen was obtained.

Example 7

Sulfonation of methane was carried out according to the procedure described afore. 0.34 mL $H_2O_2$ (aqueous solution, 70 wt. % $H_2O_2$) were added to 102.01 g oleum (32 wt. % $SO_3$) under cooling to 12-16° C. and stirring. 91.22 g of the mixture were transferred into the autoclave. After rendering inert, a pressure of 100 bar was set with gas 7. The composition of the employed gas is given in Table 1 (gas composition 7). Setting the temperature to 50° C. (at a rate of 0.5° C./min), the pressure increased to approx. 110 bar. After 3.25 h the pressure dropped by about 26 bar. 94.10 g of a non-fuming slightly yellow liquid was recovered from the autoclave. The methanesulfonic acid content was determined as 32.9 wt. % referring to a yield of 94±2%.

Example 8—Comparative

Sulfonation of methane was carried out according to the procedure described afore. 0.34 mL $H_2O_2$ (aqueous solution, 70 wt. % $H_2O_2$) were added to 99.27 g oleum (32 wt. % $SO_3$) under cooling to 12-16° C. and stirring. 88.87 g of the mixture were transferred into the autoclave. After rendering inert, an ethane pressure of 3 bar was applied (gas composition 10, Table 1), followed by addition of gas 1 (Table 1) up to a total pressure pressure of 100 bar. The composition of the employed gas is given in Table 1 (gas composition 8). Setting the temperature to 50° C. (at a rate of 0.5° C./min), the pressure increased to approx. 112 bar. After 19 h the pressure dropped by about 0.8 bar. 87.6 g of a fuming, red liquid was recovered from the autoclave. The methanesulfonic acid content was not determined. A color index in Hazen could not be obtained as the solution was out of HAZEN scale.

Example 9—Comparative

Sulfonation of methane was carried out according to the procedure described afore. 0.34 mL $H_2O_2$ (aqueous solution, 70 wt. % $H_2O_2$) were added to 102.7 g oleum (32 wt. % $SO_3$) under cooling to 12-16° C. and stirring. 91.62 g of the mixture were transferred into the autoclave. After rendering inert, a propane pressure of 3 bar (gas 11, Table 1) was applied, followed by addition of gas 1 (Table 1) up to a total pressure pressure of 100 bar. The composition of the employed gas is given in Table 1 (gas composition 9). Setting the temperature to 50° C. (at a rate of 0.5° C./min), the pressure increased to approx. 111 bar. After 18 h no further pressure drop was observed. 88.76 g of a fuming, orange-red liquid was recovered from the autoclave. The methanesulfonic acid content was not determined. A color index in Hazen could not be obtained as the solution was out of HAZEN scale.

The invention claimed is:

1. A process for manufacturing a methanesulfonic acid, the process comprising:
   preparing an initiator composition comprising reacting aqueous hydrogen peroxide with alkanesulfonic acid and/or $H_2SO_4$;
   reacting the initiator composition with sulfur trioxide and methane to form methanesulfonic acid,
   wherein the methane in the step of reacting the initiator composition has a purity of at least 98.0 mol-%, and
   wherein the methane has a maximum content of hydrocarbons of 500 ppm.

2. The process of claim 1, wherein the methane in the step of reacting the initiator composition has a purity of at least 98.5 mol-%.

3. The process of claim 1, wherein the initiator composition in the preparing further comprises sulfur trioxide.

4. The process of claim 1, wherein the initiator composition in the preparing further comprises a recycle stream from a bottom purge of a distillation of methanesulfonic acid comprising methanesulfonic acid and sulfuric acid.

5. The process of claim 1, wherein the step of reacting the initiator composition is a radical reaction.

6. The process of claim 1, wherein the methanesulfonic acid in the step of reacting the initiator composition has an HAZEN number of less than 300.

7. The process of claim 1, further comprising:
   purifying the methanesulfonic acid obtained from the step of reacting the initiator composition.

8. The process of claim 7, wherein the purifying is a single step distillation or a multi step distillation.

9. The process of claim 7, wherein the purifying is a crystallization followed by a solid-liquid separation.

10. The process of claim 7, wherein the methanesulfonic acid obtained from the purifying has an HAZEN number of less than 300.

11. The process of claim 7, wherein the preparing is conducted in a reactor A,
wherein the step of reacting the initiator composition is conducted in a reactor B or a set of reactors B, and
wherein the purifying is conducted in a column or set of columns C, and
wherein the reactor A, reactor B or set of reactors B, and column C are connected to conduct the process for the manufacturing of methanesulfonic acid continuously.

12. The process of claim 7, wherein the purifying is conducted in a distillation unit,
wherein the preparing is conducted in a reactor A,
wherein the step of reacting the initiator composition is conducted in a reactor B or a set of reactors B, and
wherein a bottom product of the distillation unit is recycled into an upstream distillation column or into the reactor A or into the reactor or set of reactors B or drained.

13. The process of claim 11, wherein the purifying is conducted in a crystallization unit,
wherein a crystallization mother liquor is recycled into the crystallization unit or into the reactor A or into the reactor B or drained.

14. The process of claim 13, wherein, further comprising, after methanesulfonic acid is obtained from the purifying:
providing methanesulfonic acid anhydride for subsequent charging of reactor A with methanesulfonic acid anhydride.

15. The process of claim 14, wherein the methanesulfonic acid anhydride in the providing comprises a separated methanesulfonic acid anhydride obtained from a further manufacturing step after the purifying or a methanesulfonic acid anhydride separated as a side-component from the purifying.

16. The process of claim 11, wherein the preparing is conducted at a temperature in a range of from −5° C. to 25° C.,
wherein the step of reacting the initiator composition is conducted at a temperature in a range of from 25° C. to 80° C., and
wherein the bottom of the column in the purifying is at a temperature in a range of from 30° C. to 220° C.

17. The process of claim 11, wherein the preparing is conducted at a pressure of at least 1013 mbar,
wherein the step of reacting the initiator composition is conducted at a pressure in a range of from 10 bar to 150 bar, and
wherein the purifying is conducted at a pressure in the column in a range of from 2 mbar to 1000 mbar.

18. The process of claim 7, wherein between the step of reacting the initiator composition and the purifying, a flash is installed.

19. The process of claim 1, wherein the methane has undergone purification in a pressure swing adsorption unit.

* * * * *